(12) United States Patent
Aldayel

(10) Patent No.: US 12,097,228 B1
(45) Date of Patent: Sep. 24, 2024

(54) MIXTURE OF CYANOBACTERIA, CHITOSAN, AND PLANT EXTRACTS FOR WOUND HEALING AND ELIMINATING PATHOGEN BACTERIA

(71) Applicant: KING FAISAL UNIVERSITY, Al-Ahsa (SA)

(72) Inventor: Munirah Fahad Aldayel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/381,542

(22) Filed: Oct. 18, 2023

Related U.S. Application Data

(62) Division of application No. 18/220,155, filed on Jul. 10, 2023.

(51) Int. Cl.
| | |
|---|---|
| *A61K 36/00* | (2006.01) |
| *A61K 9/00* | (2006.01) |
| *A61K 31/722* | (2006.01) |
| *A61K 35/02* | (2015.01) |
| *A61K 35/748* | (2015.01) |
| *A61P 17/02* | (2006.01) |

(52) U.S. Cl.
CPC .......... *A61K 35/748* (2013.01); *A61K 9/0014* (2013.01); *A61K 31/722* (2013.01); *A61K 35/02* (2013.01); *A61P 17/02* (2018.01)

(58) Field of Classification Search
None
See application file for complete search history.

(56) References Cited

U.S. PATENT DOCUMENTS

2016/0095881 A1    4/2016    Sen

FOREIGN PATENT DOCUMENTS

| CN | 111135337 B | 3/2022 |
| RU | 2489147 C2 | 8/2013 |

OTHER PUBLICATIONS

Roell et al. (2017) Frontiers in Pharmacology, vol. 8: Article 158 (11 pages). (Year: 2017).*
Tallrida (2011) Genes & Cancer 2(11): 1003-1008. (Year: 2011).*
Agarwal et al. (2007) Phytother. Res. 21; 401-405 (Year: 2007).*
Asghari et al. (2016) J. Appl. Biotech. Rep. vol. 3, Issue 1, 345-351. (Year: 2010).*
Xie et al. (2001) Bioorganic and Med. Chem. Lett. 11: 1699-1701. (Year: 2001).*
Gunes, S. et al., "In vitro evaluation of Spirulina platensis extract incorporated skin cream with its wound healing and antioxidant activities", Pharmaceutical Biology 55(1): pp. 1824-1832 (2017).
Do, N.H.N., "Recent Developments in Chitosan Hydrogels Carrying Natural Bioactive Compounds," Carbohydrate Polymers 294:119726 (2022).

* cited by examiner

*Primary Examiner* — Russell G Fiebig
(74) *Attorney, Agent, or Firm* — Nath, Goldberg & Meyer; Joshua B. Goldberg

(57) ABSTRACT

A combination of cyanobacteria, chitosan, and plant extracts for wound healing, eliminating pathogen bacteria, or promoting antioxidant activity is provided. The cyanobacteria my be a *Spirulina platensis* extract and the plant extract may be shilajit.

2 Claims, 3 Drawing Sheets

MIXTURE OF CYANOBACTERIA, CHITOSAN, AND PLANT EXTRACTS FOR WOUND HEALING AND ELIMINATING PATHOGEN BACTERIA

CROSS-REFERENCE TO RELATED APPLICATION

This application is a divisional of U.S. patent application Ser. No. 18/220,155, filed on Jul. 10, 2023, the entire contents of which are incorporated herein by reference.

BACKGROUND

1. Field

The present disclosure relates to the use of a combination of cyanobacteria, chitosan, and plant extracts for wound healing and eliminating pathogen bacteria.

2. Description of the Related Art

Chitosan is a linear polysaccharide consisting of 1-4 linked d-glucosamine (deacetylated and acetylated units) of N-acetyl-d-glucosamine. It used widely in industrial and medicinal applications. Chitosan is produced from the shell of shrimp, some fungi, seashells, and other marine crustaceans and is widely used for multiple purposes (Wansapura et al., 2017; Sami et al., 2021b; Kumar. N and Neeraj, 2019). Chitosan is commonly used as an agent against a wide scope of microorganism's cellular components.

Polysaccharide components have excellent properties, including being nontoxic, showing antioxidant, antimicrobial, and antifungal activity, and exhibiting good nutrient profiles (Kumar. N and Neeraj, 2019). This results in microbial death caused by the hydrolysis of peptidoglycans, including intracellular electrolytes (Rokayya et al., 2021; Sami, et al., 2021a). Chitosan has the ability for wound healing (Azuma, K et al., 2018). Also, a specific cyanobacteria, *Spirulina platensis*, has the ability to heal wounds and inhibit pathogenic bacteria.

Shilajit, also known as "Moomiyo," is found in the high altitudes of the Himalayan Mountains and is considered as one of the "wonder medicines" of Ayurveda, the traditional Indian system of medicine dating back to 3500 B.C.E. Shilajit is regarded as one of the most important components in the Ayurvedic System of medicine and is also used as an adaptogen. S. Ghosal et al., Shilajit I: chemical constituents, 65 J. PHARM. SCI. 772 (1976); C. Velmurugan et al., Evaluation of safety profile of black shilajit after 91 days repeated administration in rats, 2 ASIAN PAC. J. TROP. BIOMED. 210 (2012). Shilajit is regarded as a "maharasa" (super-vitalizer) in Ayurveda. Shilajit is composed of rock humus, rock minerals, and organic substances that have been compressed by layers of rock mixed with marine organisms and microbial metabolites. Shilajit oozes out of the rocks in the Himalayas at higher altitudes ranging from 1000 to 5000 meters as black mass, as the rocks become warm during summer. C. Velmurugan et al., supra at 210. Shilajit contains fulvic acids ("FAs") as its main components, along with dibenzo-a-pyrones ("DBPs") and DBP chromoproteins, humic acid, and more than forty (40) minerals.

To date, the ability to heal wounds, and treatments for the same, is in need of improvement, particularly for various chronic wounds. Such wounds can often be difficult to treat due to lack of a sufficient oxygen supply and the ease to infection, therefore making healing difficult. Further, most if not all current products used in wound dressings are disposable, and need to be replaced completely after use, causing undue waste.

The development of a new treatment for wound healing and inhibiting pathogenic bacteria solving the aforementioned problems is desired.

SUMMARY

The present subject matter relates to treatments for wound healing and inhibiting pathogenic bacteria comprising a cyanobacteria including, by way of non-limiting example, *Spirulina platensis*, chitosan, and a plant extract. Such treatments can have an effect in healing wounds, eliminating wounds, and inhibiting pathogen bacteria.

In an embodiment, the present subject matter relates to a method of promoting wound healing in a subject, the method comprising administering to a subject in need thereof a topical composition comprising a cyanobacteria, chitosan, a plant extract, and a topically acceptable carrier.

In another embodiment, the present subject matter relates to a method of promoting antioxidant activity in a subject, the method comprising administering to a subject in need thereof a topical composition comprising a cyanobacteria, chitosan, a plant extract, and a topically acceptable carrier.

In a further embodiment, the present subject matter relates to a topical composition comprising a cyanobacteria, chitosan, a plant extract, and a topically acceptable carrier.

These and other features of the present subject matter will become readily apparent upon further review of the following specification.

BRIEF DESCRIPTION OF THE DRAWINGS

FIGS. 2A-2C depict images displaying the effect of topical application of: FIG. 2A) cyanobacteria, FIG. 2B) chitosan, and FIG. 2C) Shilajit individually on excision wound healing progression obtained from the experimental groups.

Similar reference characters denote corresponding features consistently throughout the attached drawings.

DETAILED DESCRIPTION OF THE PREFERRED EMBODIMENTS

Figure 1:
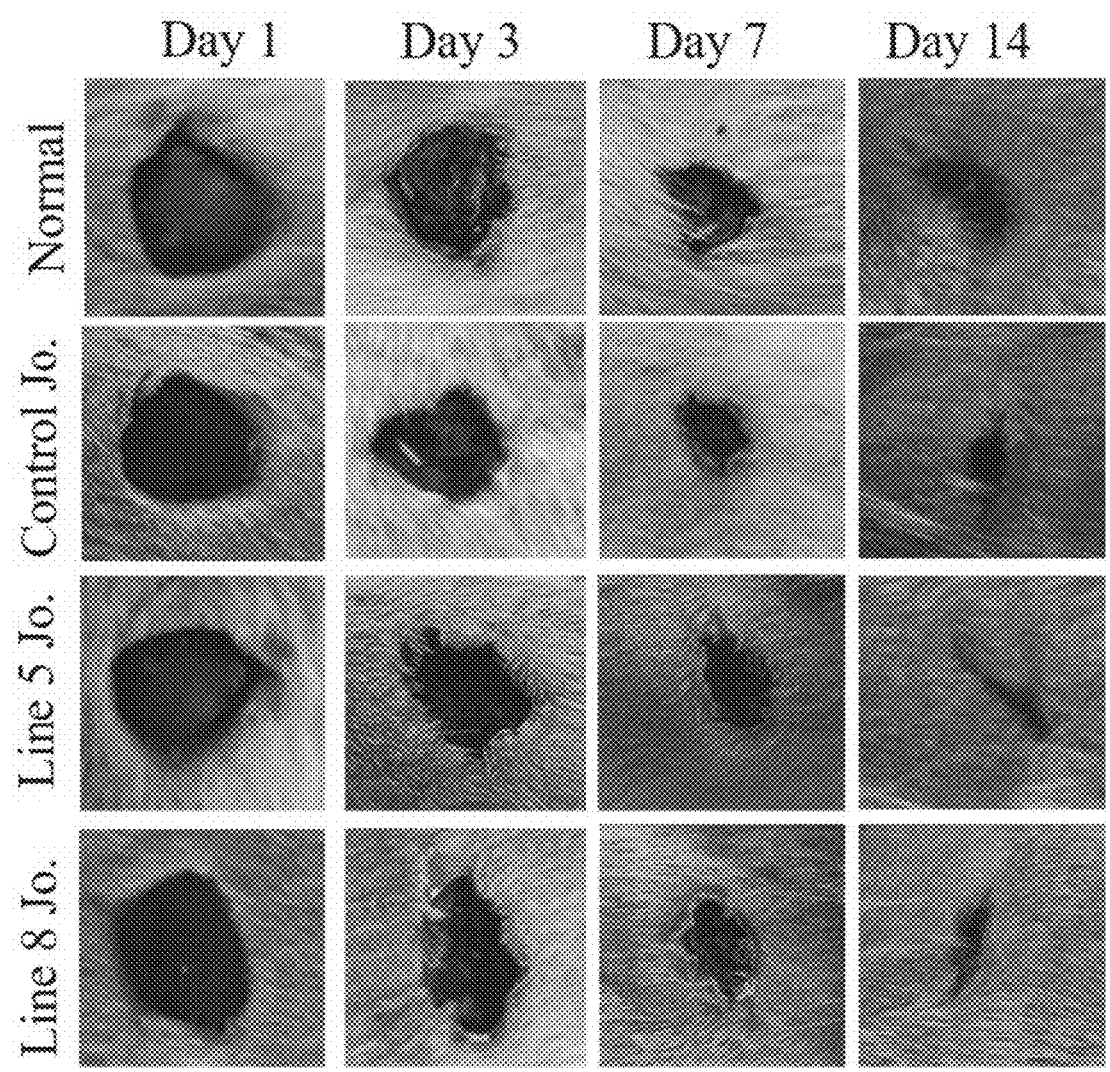
FIG. 1 depicts images displaying the effect of a mixture of cyanobacteria, chitosan, and Shilajit topical application on excision wound healing progression obtained from the experimental groups.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a wound in need of healing.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a method of promoting wound healing in a subject, the method comprising administering to a subject in need thereof a topical composition comprising a cyanobacteria, chitosan, a plant extract, and a topically acceptable carrier.

In certain embodiments in this regard, the cyanobacteria can comprise, by way of non-limiting example, a *Spirulina platensis* extract. Similarly, the plant extract can comprise, by way of non-limiting example, shilajit.

In one embodiment, the cyanobacteria, the chitosan, and the plant extract can act synergistically to promote wound healing.

In another embodiment, the topical composition can be topically administered to a site of the wound on the subject. In this regard, the topical composition can be topically administered once per day to the site of the wound on the subject.

In a further embodiment, the once per day topical administration of the topical composition can further prevent bacterial infection in the subject. Similarly, the once per day topical administration of the topical composition can further eliminate pathogenic bacteria at the site of the wound on the subject.

In an embodiment, the once per day topical administration of the topical composition can provide about 84% to about 91% wound contraction within about 14 days of commencement of the topical administration. In this regard, the once per day topical administration of the topical composition can provide about 88% wound contraction within about 14 days of commencement of the topical administration. Further, the once per day topical administration of the topical composition can provide about 100% wound contraction within about 21 days of commencement of the topical administration.

In still another embodiment, the once per day topical administration of the topical composition can provide an about 15-day epithelization period.

In another embodiment, the present subject matter relates to a method of promoting antioxidant activity in a subject, the method comprising administering to a subject in need thereof a topical composition comprising a cyanobacteria, chitosan, a plant extract, and a topically acceptable carrier.

In a further embodiment in this regard, the administration of the topical composition can further promote anti-inflammatory activity in the subject.

In a further embodiment, the present subject matter relates to a topical composition comprising a cyanobacteria, chitosan, a plant extract, and a topically acceptable carrier.

In an embodiment, the cyanobacteria in the topical composition can comprise, by way of non-limiting example, a *Spirulina platensis* extract. In this regard, the *Spirulina platensis* may be chosen because it contains a high proportion of diverse proteins, including specific functional and structural proteins that not only prevent bloodshed, but also act fast in healing and formatting different layers of the skin. An extract of the *Spirulina platensis* may be used because it contains a high proportion of diverse proteins in a molecular weight of 100 Da.

Similarly, the plant extract in the topical composition can comprise, by way of non-limiting example, shilajit, such as shilajit oil. In an alternative non-limiting example, the plant extract can be pumpkin oil.

In certain embodiments, the cyanobacteria, the chitosan, and the plant extract can be present in the topical composition in synergistic amounts. In this regard, the cyanobacteria, the chitosan, and the plant extract can be present in the topical composition in synergistic amounts for promoting wound healing.

In an alternative embodiment, the chitosan in the topical composition can form a hydrogel.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compositions can be typically administered at a therapeutically or pharmaceutically effective dosage, e.g., a dosage sufficient to provide treatment for wound healing. Administration of the compositions is typically done topically.

The present compositions can be in various topical dosage forms such as ointments, gels, creams, lotions, foams, aerosols, and the like. The present compositions can be mixed under sterile conditions with a topically acceptable carrier and, if required, any needed preservatives, buffers, or propellants. The composition can be presented in a form suitable for daily, weekly, or monthly administration. The pharmaceutical compositions herein will contain an amount of the active ingredients necessary to deliver an effective dose. A therapeutically effective amount of the topical formulation or an amount effective to treat a condition, such as a wound in need of healing, may be determined initially from the Examples described herein and adjusted for specific targeted conditions using routine methods.

Generally, the topical composition will contain about 0.1% to 90%, for example about 0.5% to 50%, by weight of the cyanobacteria, chitosan, and plant extract, the remainder being suitable pharmaceutical excipients, carriers, etc. In an embodiment, the topical composition can contain about 2% by weight of the cyanobacteria, chitosan, and plant extract.

The present subject matter can be further understood by referring to the following examples.

EXAMPLES

Example 1

Procedure for Administration of Topical Compositions

Ketamine (100 mg/kg) and xylazine (10 mg/kg) were intraperitoneally administered for anesthesia. Rats' dorsal fur was clipped with an electric razor, and the wound sites were cleaned with 70% ethanol. Next, a 2 cm excision wound with a circular area of 4 $cm_2$ was created on the rat's back skin towards the posterior surface of the neck using a scalpel blade. The rats were housed individually in metabolic cages following the procedure.

Rats that had been subjected to surgery were randomly divided into five groups (n=6). The initial group served as a control group and in which the animals received no treatment. The second batch of animals received 2% cream mixture (w/w) comprising cyanobacteria, chitosan, and shilajit treatment. The third, fourth, and fifth groups, included mice which received treatments with cyanobacteria, chitosan, or shilajit (2% w/w) alone, respectively.

To create a basic ointment, various material preparations were made in Vaseline 2% (w/w). During the course of the trial, the ointment mixtures were applied topically to the wound once per day (following the procedures in Bahram-soltani et al., 2017). Direct application of the prepared combination ointments to the open wound continued until the skin had fully healed. No antibiotics were given, and the rats were routinely checked for infections. The shrinkage of the wound area was documented using a digital camera (Canon Inc., Tokyo, Japan).

Example 2

Effects on Wound Healing

As seen in FIG. 1, the images display the effect of the mixture of cyanobacteria, chitosan, and Shilajit topical application on the excision wound healing progression obtained from the experimental groups. The results of these experiments were quantified as shown below in Table 1.

| Groups | Wound contraction % | | | | Epithelialization period |
| --- | --- | --- | --- | --- | --- |
| | $3^{rd}$ Day | $7^{th}$ Day | $14^{th}$ Day | $21^{st}$ Day | (Days) |
| Control | 11.33 ± 1 | 28.88 ± 2.22 | 62.99 ± 3 | 89.3 ± 3.58 | 20.05 ± 1.44 |
| Treated | 16.66 ± 1.8* | 57.16 ± 1.63 * & | 87.93 ± 3.56 * & | 100 | 15.0 ± 0.41 * & |

All values shown in Table 1 are expressed as mean±SD (n=6). * specifies statistically significant from normal untreated group, & specifies statistically significant from Control ($p<0.05$) using one-way ANOVA followed by Tukey's test as a post hoc analysis.

Figure 2A:
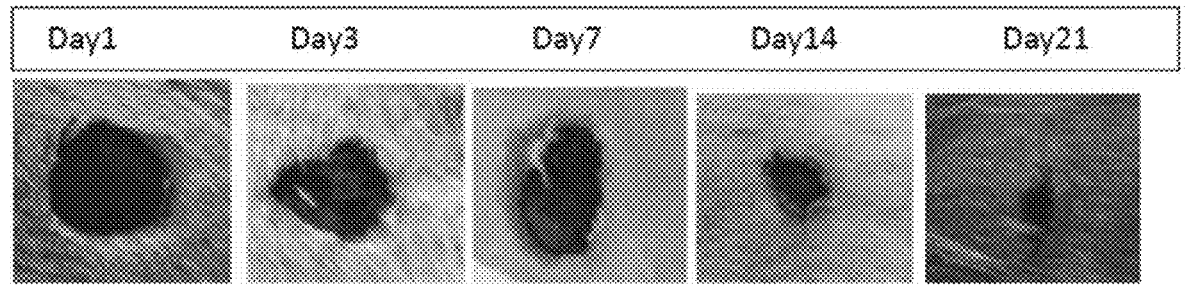
Figure 2B:
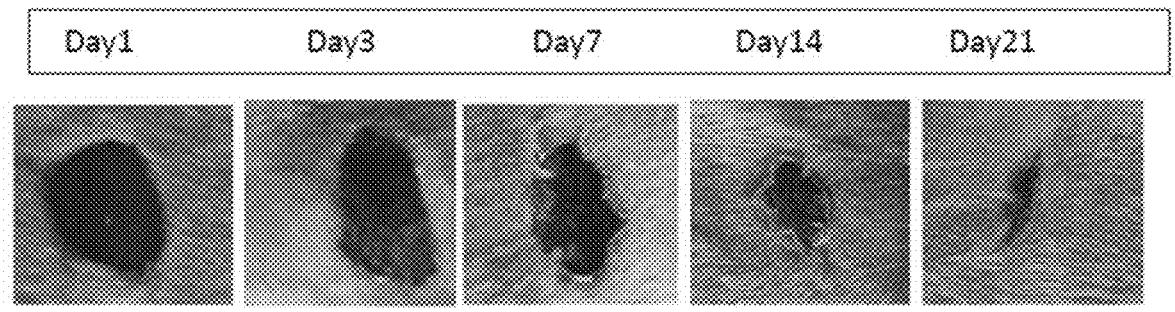
Figure 2C:
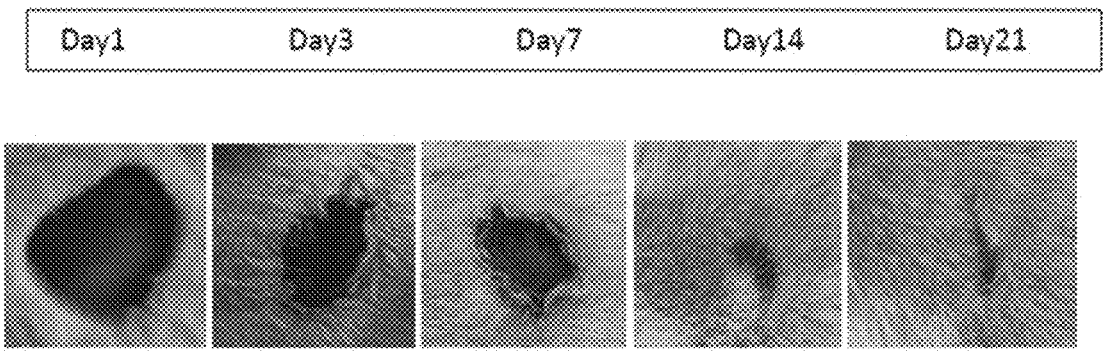

As seen in FIGS. 2A-2C, the images display the impact of cyanobacteria (2A), chitosan (2B) and Shilajit (2C) individually. These results illustrate that the cyanobacteria, chitosan, and Shilajit help wound healing but take a long time to recover, i.e., within 21 days, whereas the mixture of cyanobacteria, chitosan, and Shilajit gave a quick recovery and wound healing within 14 days.

Example 3

Anti-Inflammatory and Antioxidant Effects

Figure 3A:
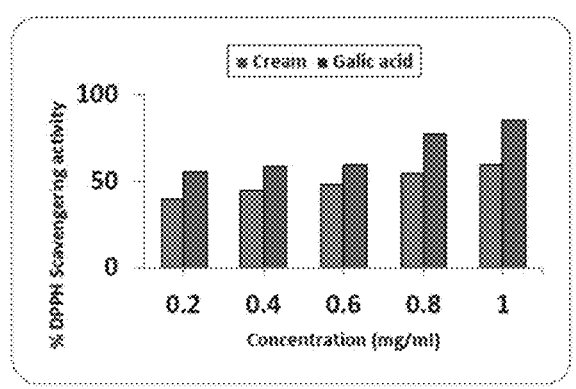
FIGS. 3A-3B are charts showing estimation of antioxidant (FIG. 3A) and anti-inflammatory (FIG. 3B) activities of topical application of a mixture of cyanobacteria, chitosan, and Shilajit.
Figure 3B:
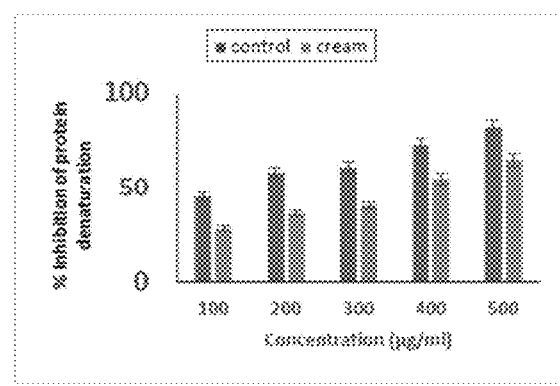

FIGS. 3A-3B show an estimation of the antioxidant and anti-inflammatory activities of the cream mixture of cyanobacteria, chitosan, and Shilajit. FIG. 2A shows an estimation 236 of DPPH radical scavenging activity from different concentrations of cream using mixture of cyanobacteria, chitosan, and Shilajit. FIG. 2B shows the anti-inflammatory activity of the mixture of cyanobacteria, chitosan, and Shilajit. Different letters indicate significant differences (p<0.05) according to Duncan's test. 239

It is to be understood that the mixture of cyanobacteria, chitosan, and plant extracts for wound healing and eliminating pathogen bacteria is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A hydrogel comprising about 2% by weight *Spirulina platensis* extract, about 2% by weight chitosan, about 2% by weight shilajit, and a topically acceptable carrier.

2. A hydrogel consisting of about 2% by weight *Spirulina platensis* extract, about 2% by weight chitosan, about 2% by weight shilajit, and a topically acceptable carrier.

\* \* \* \* \*